(12) United States Patent
Pratt

(10) Patent No.: US 8,001,853 B2
(45) Date of Patent: Aug. 23, 2011

(54) CONDITIONING CHAMBER FOR METALLURGICAL SURFACE SCIENCE

(75) Inventor: Allen Pratt, Ottawa (CA)

(73) Assignee: Her Majesty the Queen in right of Canada, as represented by the Minister of Natural Resources, Ottawa, Ontario (CA)

( * ) Notice: Subject to any disclaimer, the term of this patent is extended or adjusted under 35 U.S.C. 154(b) by 558 days.

(21) Appl. No.: 11/979,461

(22) Filed: Nov. 2, 2007

(65) Prior Publication Data

US 2008/0173108 A1    Jul. 24, 2008

Related U.S. Application Data

(63) Continuation-in-part of application No. 11/115,274, filed on Apr. 27, 2005, which is a continuation-in-part of application No. 10/259,747, filed on Sep. 30, 2002.

(51) Int. Cl.
*G01N 1/00* (2006.01)
(52) U.S. Cl. .......................................... 73/863; 73/865.8
(58) Field of Classification Search ........................ None
See application file for complete search history.

(56) References Cited

U.S. PATENT DOCUMENTS

| | | | | |
|---|---|---|---|---|
| 3,720,829 A | * | 3/1973 | Palmberg | 250/440.11 |
| 4,904,141 A | | 2/1990 | Contin | |
| 5,033,720 A | | 7/1991 | Chen | |
| 5,139,383 A | | 8/1992 | Polyak et al. | |
| 5,200,136 A | | 4/1993 | Ramaseder et al. | |
| 5,518,595 A | | 5/1996 | Hosokawa et al. | |
| 5,954,489 A | | 9/1999 | Kinoshita | |

* cited by examiner

*Primary Examiner* — Robert R Raevis
(74) *Attorney, Agent, or Firm* — Flynn, Thiel, Boutell & Tanis, P.C.

(57) ABSTRACT

The present invention provides a conditioning chamber device and a conditioning method for metallurgical samples which can be directly connected to an instrument having an examination chamber operable in an ultra high vacuum (UHV) condition at a selected pressure below $10^{-7}$ Torr. The conditioning chamber comprises at least one vacuum pump means to reduce the conditioning chamber to the selected UHV condition corresponding to the selected pressure of the examination chamber; sample retaining means; at least one fracturing means to prepare an analysis surface on the sample; sample drying means for slow drying the sample in the selected UHV condition; a sealable outlet constructed and arranged to be operatively connected to the inlet of the examination chamber; and transporting means to transport the sample after surface preparation through a connecting means into the examination chamber without leaving the selected ultra high vacuum condition.

22 Claims, 4 Drawing Sheets

CONDITIONING CHAMBER FOR METALLURGICAL SURFACE SCIENCE

This is a Continuation-in-part of U.S. patent application Ser. No. 11/115,274, filed Apr. 27, 2005, which is a continuation-in-part of U.S. patent application Ser. No. 10/259,747, filed Sep. 30, 2002.

FIELD OF THE INVENTION

This invention relates to conditioning chambers for preparation of metallurgical samples for examination and analysis.

BACKGROUND OF THE INVENTION

Metallurgical processing for surface science research typically involves the examination of a sample in a vacuum chamber of an examination instrument, generally in an ultra high vacuum (UHV) condition, which can be defined as a pressure which is below $10^{-7}$ Torr, and may be down to $10^{-9}$ Torr, or lower. Typically, samples are prepared for such research in separate instruments, before an appropriate sample is introduced to a UHV examination chamber.

Such preparation typically involves one or both of two important stages, comprising (1) drying and (2) fracturing, each of which presents problems.

In the drying stage, metallurgical samples, which are generally wet, can be dried for analysis by various known methods, which include drying in an inert gas environment in a suitable container. Another known method is drying in a forechamber which is available as an attachment to known examination instruments. This method, developed at the Ian Wark Institute in Adelaide, Australia, is described in the text Minerals Engineering, 1991, Smart, R. St. C., vol. 4, pp. 891-909.

There are problems arising from the use of either of these two principal known methods of drying samples for analysis.

In relation to the first method, where a sample is dried in an inert atmosphere not directly connected to the examination instrument, there are risks of adverse effects during transport to the instrument, including from air exposure.

However, in relation to the second method, i.e. where a sample is not dried in a remote location, but in a forechamber to the instrument, or in the examination chamber itself, although the air exposure risk is reduced or removed, there are two important disadvantages. Firstly, there is a risk of adverse effect on the UHV conditions of the examination chamber when the sample is moved into that chamber; and secondly, there is the problem that arises from the length of time required for preparation of such samples in the forechamber. Although a typical forechamber is designed to be pumped down to the desired vacuum condition in a relatively short period, of approximately twenty minutes, the process is of necessity substantially longer, often many hours, for proper preparation of metallurgical samples. While such samples are in the forechamber, or the examination chamber itself, the examination chamber cannot be accessed for other work, and valuable instrument time is thus lost.

In the second stage of sample preparation for surface science research, i.e. the fracturing of the sample to obtain a suitable surface for analysis, the methods currently in use also raise problems.

For example, U.S. Pat. No. 3,720,829 to Palmberg teaches the fracturing of samples within an examination chamber to be operated in a high vacuum condition. As the vacuum of the chamber is broken each time that a sample is placed in the chamber, the vacuum level is required to be repeatedly reestablished. Even to attain only a high vacuum condition, rather than the UHV condition of the present invention, can take several days, during which the examination chamber could not be used for other purposes.

Further problems arise in relation to the fracturing method itself. Typically, current methods of fracturing involve a high energy impact, for example impact by the use of a hammer and chisel in a UHV chamber, after freezing of the sample to an extremely low temperature, generally below 75 K. However, if this method is used for a brittle material, the entire sample can be destroyed. If instead fracturing is performed in an inert gas in a location which is remote from the examination instrument, there is a serious risk of contamination during transfer to that instrument, the risk being increased by the more reactive nature of the surfaces which have been exposed by fracture. Further limiting factors at this stage include the shape and size of samples.

Typically also, a single chisel is used, which is generally effective in many situations. However, it has been found that for metallurgical samples, greater effectiveness and precision can be achieved, without high impact and without any manifest disadvantages, by the use of a pair of chisels, preferably in opposed directions in relation to each other.

It has been found that a UHV conditioning chamber can be provided which can be attached to, and directly connected with, a UHV examination chamber; and in which a sample can be prepared by drying and fracturing for subsequent transfer into the examination chamber, without leaving the desired UHV condition, thereby avoiding the problems associated with the extended drying time which may be required, and with the risks presented by transfer from a remote drying location to the examination chamber.

It has also been found that the use of vacuum pumps of more than one type can improve the attainment of the desired UHV condition. It has further been found that the use of appropriate retaining means within the chamber can enable the use of dual chisels for fracturing, with consequent improved quality and reduced risk of damage to the sample during fracturing. Further, it has been found that the retaining means for the sample within the conditioning chamber can be combined with suitable transporting means to move the prepared sample into the examination chamber of an instrument through a connecting means.

The invention seeks to provide a conditioning chamber, and a method of conditioning samples in a conditioning chamber, which is suitable for samples of irregular shapes, a wide range of sizes, and different conditions, including slurry conditions. The condition chamber includes an improved UHV environment for drying metallurgical samples for analysis in UHV instruments, and in which the surface preparation by fracturing can also be performed, thus minimizing the risks of contamination from exposure to air or other changed conditions during transfer.

The invention further seeks to provide improved sample retaining and fracturing means which substantially reduce or eliminate the risk of destruction of or damage to samples during the fracturing process.

SUMMARY OF THE INVENTION

The present invention therefore seeks to provide a conditioning chamber device for metallurgical samples, constructed and arranged to be operatively connected to an instrument having an examination chamber operable in an ultra high vacuum condition at a selected pressure below $10^{-7}$ Torr and having a sealable inlet, the conditioning chamber comprising (i) at least one vacuum pump means constructed and arranged to reduce the conditioning chamber to a selected ultra high vacuum condition at a pressure below $10^{-7}$ Torr and corresponding to the selected pressure of the examination chamber;

(ii) a sample retaining means;

(iii) at least one fracturing means constructed and arranged to prepare on a sample a surface suitable for metallurgical analysis;

(iv) a drying means constructed and arranged for slow drying of the sample in the selected ultra high vacuum condition;

(v) a sealable outlet constructed and arranged to be operatively connected to the inlet of the examination chamber; and (vi) a transporting means to transport the sample after surface preparation through a connecting means into the examination chamber without leaving the selected ultra high vacuum condition.

The invention further seeks to provide a method of conditioning a metallurgical sample for surface analysis by the steps of (i) providing a conditioning chamber device operatively and sealably connectable to an instrument having an examination chamber operable in an ultra high vacuum condition at a selected pressure below $10^{-7}$ Torr, (ii) securing the sample within the conditioning chamber;

(iii) reducing the conditioning chamber to a selected ultra high vacuum condition corresponding with the selected pressure of the examination chamber;

(iv) drying the sample;

(v) fracturing the sample by a fracturing means to prepare a surface suitable for metallurgical analysis; and (vi) transporting the sample by a transporting means from the conditioning chamber into the examination chamber without leaving the selected ultra high vacuum condition.

In the conditioning chamber device of the invention, an enclosed conditioning chamber is provided which is attachable to a commercially available examination instrument having an ultra high vacuum instrument chamber. Within the conditioning chamber, a metallurgical sample of regular or irregular shape and in any typical condition can be retained by a suitable means, while the conditioning chamber is gradually reduced to the desired vacuum condition, by the use of at least one vacuum pump.

Preferably, the sample retaining means is a pedestal, on which a sample can be secured, either directly or on a suitable sample platen or other container. More preferably, the sample retaining means further includes a gripper which is designed to retain the pedestal in the desired position throughout the conditioning process.

To facilitate movement of the sample after the conditioning process is complete, transporting means is provided, preferably a transporter rod, which is securely attached, and preferably permanently affixed, to the gripper or other retaining means. Most preferably, the transporter rod is contained within a tube, attached to the outside of the housing of the conditioning chamber. A magnetic sleeve surrounding the tube along part of its length is magnetically coupled with the transporter rod, such that movement of the sleeve will direct the rod along the axial direction of the tube. Such movement of the rod thus effects the desired movement of the sample retaining means, with the sample, in particular for transporting the sample out of the conditioning chamber to the examination chamber of an examination instrument, as described below.

For reducing the pressure in the conditioning chamber to the desired level, preferably more than one type of pump is used. More preferably the pumping is performed in sequence by a low vacuum roughing pump, a turbomolecular pump and an ion pump.

Preferably, the low vacuum roughing pump is selected from a rotary vane pump, a dry scroll pump and a diaphragm pump, and the ion pump is selected from a triode ion pump, a diode ion pump and a star cell ion pump.

After the conditioning chamber has been reduced to the desired vacuum condition, and the sample has been dried to the required state, it can be fractured by suitable means, such as chisels. Preferably these are provided as a pair of chisels operating in opposed directions in relation to each other, which most preferably have a cutting edge of tempered steel.

The conditioning chamber device is attachable to a commercially available examination instrument having an ultra high vacuum examination chamber, the attachment being in such manner as to enable the device to operate without interference with the instrument itself or with its operation, or with a forechamber or other attachments which may already be attached to the examination instrument.

The conditioning chamber device is provided with a connecting means through which, after completion of the conditioning process, and fracturing to provide a suitable surface for analysis, the prepared sample can be transferred into the examination chamber. The connecting means is suitably sealed so that the transfer can be effected without loss of vacuum or any risk of contamination of the sample from contact with outside air. Once the sample is in the examination chamber of the instrument, it can be subjected to the desired analysis.

BRIEF DESCRIPTION OF THE DRAWINGS

The invention will now be described by way of reference to the drawings, in which.

DETAILED DESCRIPTION OF THE PREFERRED EMBODIMENT

Figure 1:
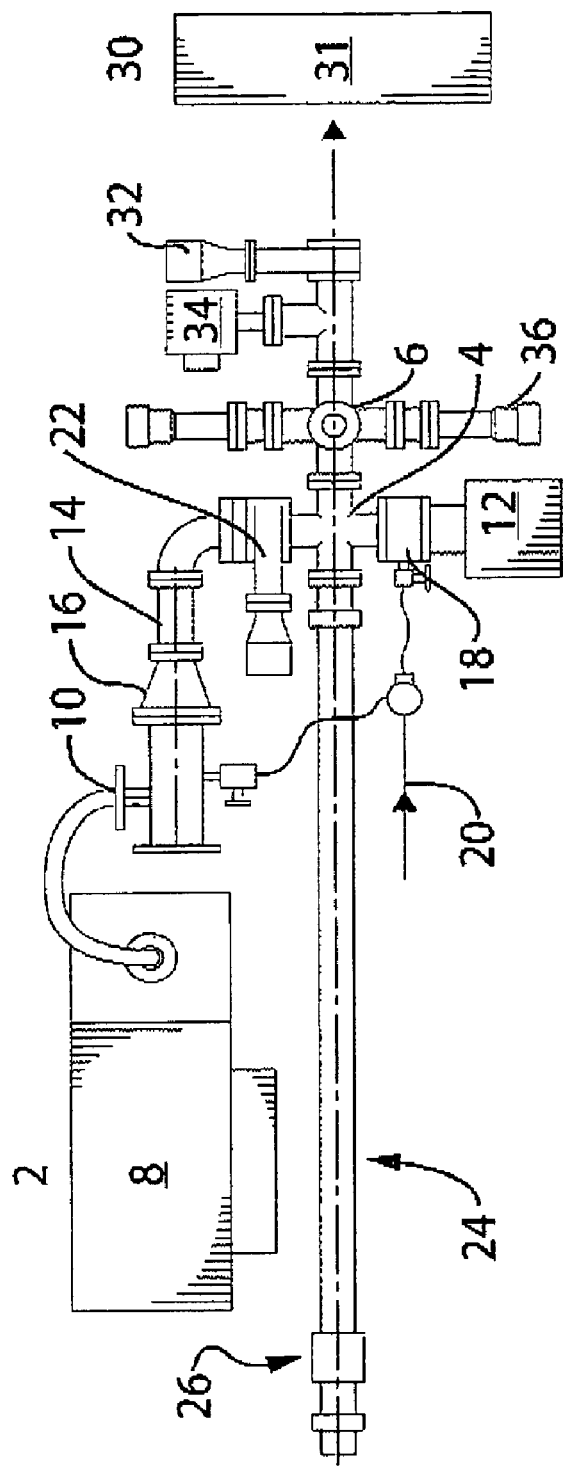
FIG. 1 is a plan view of an embodiment of the invention.

Referring to FIG. 1, a conditioning chamber device 2 comprises a housing 4, enclosing a chamber 6 which can be brought to an ultra high vacuum (UHV) condition, at or below $10^{-7}$ Torr. To achieve this condition, a low vacuum roughing pump 8, a turbomolecular pump 10 and an ion pump 12 are provided which are operable in sequence. The pumps 8, 10 and 12 are connected to the chamber 6 by suitable known linkage components (not specifically identified). As shown in FIG. 1, the first two pumps 8 and 10 are located so as to be connected to the chamber 6 by a first gate valve 22, and the third pump 12 is located so as to be connected to the chamber 6 at a second location, shown in FIG. 1 as adjacent to an up-to-air valve 18, and on the opposite side of the chamber 6 from the connection of the first two pumps 8 and 10. However, any suitable arrangement of the pumps 8, 10 and 12 can be selected such that the pumps can be operated and controlled effectively. Inert gas connection lines 20 for venting the chamber 6 are provided.

Figure 2:
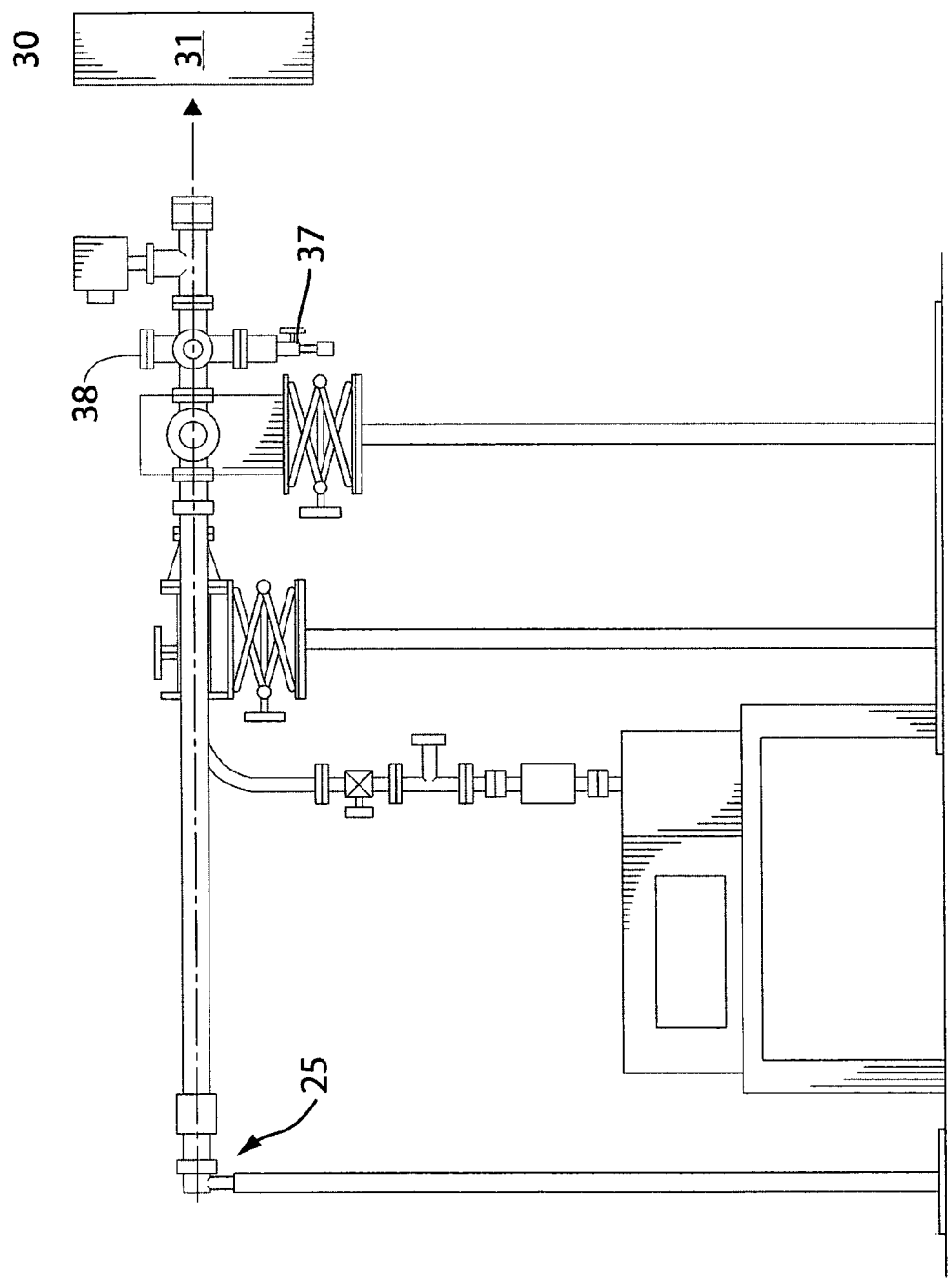
FIG. 2 is a side elevation view of the embodiment shown in FIG. 1.

Attached to the housing 4, at a suitable location selected to avoid interference with the connection of the pumps 8, 10 and 12, is a cylindrical tube 24, supported at a free end 25 (shown in FIG. 2). A cylindrical magnetic sleeve 26 surrounds the tube 24 along part of its length, and is movable along the length of the tube 24 such that the magnetic force can move a transporter rod 28, (shown in FIG. 3) which is magnetically coupled with the magnetic sleeve 26, and contained within the tube 24, the direction of movement being along the axial direction of the tube 24.

The chamber 6, at a location opposed to the connection of the tube 24 with the chamber 6, is provided with connection means for attachment to an examination instrument 30. The chamber 6 is provided with a second gate valve 32, having suitable controls including vacuum gauge 34. Adjacent to the second gate valve 32, the conditioning chamber device 2 can be attached by suitable further connection means (not shown) to the examination instrument 30, such that in an open position the interior of the chamber 6 can be directly connected to the examination chamber 31 of the examination instrument 30.

At each side of the housing 4, horizontal linear motion feeders 36 are provided, to effect horizontal movement of the fracturing means in relation to the sample (discussed in relation to FIGS. 3 and 4 below) within the chamber 6. Similarly, vertical linear motion feeder 37 (shown in FIG. 2) is provided below the housing 4, to effect vertical movement of the sample retaining means to adjust its position as desired within the chamber 6.

Referring to FIGS. 1 and 2, a sealable access flange 38 is provided at the upper region of the housing 4 to enable the placement of a sample (not shown in FIGS. 1 and 2) within the chamber 6.

Figure 3:
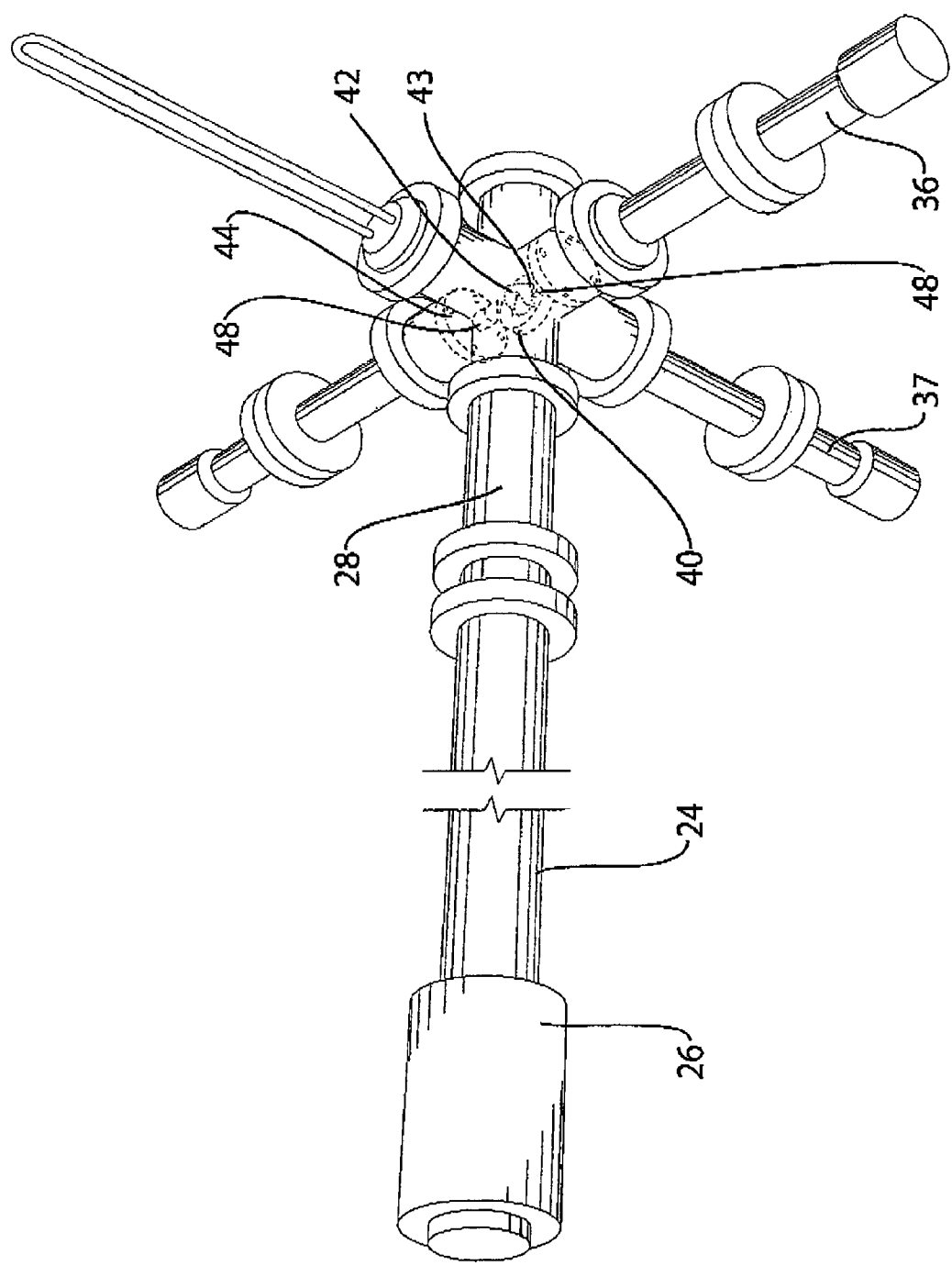
FIG. 3 is an isometric view of the retaining, fracturing and transporting means of the embodiment shown in FIG. 1.
Figure 4:
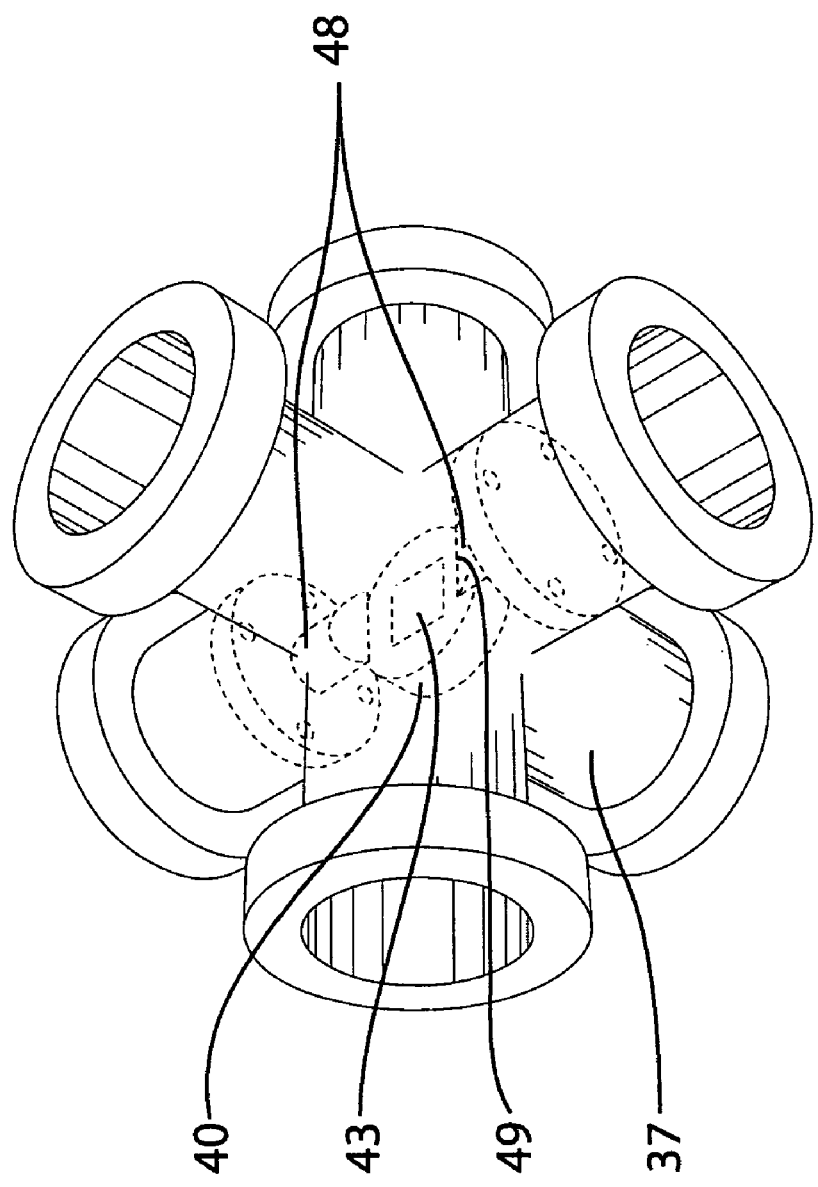
FIG. 4 is an enlarged view of the retaining and fracturing means of the embodiment shown in FIG. 3.

Referring to FIGS. 3 and 4, a sample 42 is placed on a sample platen 43, which in turn is secured to a pedestal 40. The pedestal 40 is retained in a desired position by a retaining means, such as gripper 44, which is securely or preferably permanently fixed to the transporter rod 28, within tube 24, and controlled by magnetic sleeve 26. The vertical height of pedestal 40 can be adjusted by vertical linear motion feeder 37. Located on each side of the sample platen 43, and regulated by horizontal linear motion feeders 36, are an opposed pair of chisels 48, having cutting edges 49, which can be brought into contact with the sample 42.

In the operation of the conditioning chamber device 2, the sample 42, secured directly, or supported by sample platen 43, to the pedestal 40, is introduced to the chamber through access flange 38. Pedestal 40 is secured in the desired position by the gripper 44, and access flange 38 is secured and capped. At this point, the second gate valve 32 is in a closed position. The chamber 6 can thus be brought to the desired UHV condition by means of the three pumps 8, 10 and 12 in sequence. The low vacuum roughing pump 8, for example a rotary vane pump, a dry scroll pump or a diaphragm, can be used to reduce the pressure to $10^{-2}$ Torr. Thereafter the turbomolecular pump 10 can be used to reduce the pressure further to $10^{-7}$ Torr. To complete the process, the ion pump 12, for example a triode ion pump, a diode ion pump or a star cell ion pump, is used to reduce the pressure to the desired level below $10^{-7}$ Torr, which will correspond to the level at which the examination chamber 31 will have been prepared prior to movement of the sample 42 into the examination chamber 31.

The timing of the pressure reduction process can be selected as desired, according to the properties of the sample 42. At this stage, the conditioning chamber device 2 is already attached to the examination instrument 30, but the chamber 6 is not internally connected with the examination chamber 31. The examination chamber 31 can thus be used for any other purposes during this time period, avoiding any unnecessary down-time for the examination chamber 31 during the sample conditioning process.

As can be more clearly seen in FIG. 4, when fracturing is required, the sample 42 can be fractured using the chisels 48, the cutting edges 49 of which are preferably made of tempered steel. Using external controls (not shown) operating on the respective elements indicated in FIG. 4, in particular the horizontal motion feeders 36, the chisels 48 are brought to the sample 42, and a suitable surface can be prepared to allow for the desired analysis.

When the fracturing of the sample 42 is complete, the chamber 6 can be internally connected to the examination chamber 31, by the opening of the second gate valve 32. The examination chamber will have been prepared to the desired UHV condition. By movement of the magnetic sleeve 26 along the tube 24, the magnetically coupled transporter rod 28 is moved in a direction along the axis of the tube 24. Thus, the sample 42, secured directly or indirectly to the pedestal 40, which in turn is still retained by the gripper 44, can be moved from the chamber 6 to the examination chamber 31, for the desired analysis process.

It can thus readily be seen that throughout the conditioning and fracturing process, there is no movement of the sample 42 itself which could result in damage, and no exposure to the risk of contamination during a transport process from a remote location to the examination chamber 31.

Each of the components of the conditioning chamber device 2 of the invention can be constructed of any suitable materials which are, or can be determined to be, compatible for operation within UHV conditions.

I claim:

1. A conditioning chamber device for metallurgical samples, constructed and arranged to be operatively connected to an instrument having an examination chamber operable in an ultra high vacuum condition at a selected pressure below $10^{-7}$ Torr and having a sealable inlet, the conditioning chamber comprising
    (i) at least one vacuum pump means constructed and arranged to reduce the conditioning chamber to a selected ultra high vacuum condition at a pressure below $10^{-7}$ Torr and corresponding to the selected pressure of the examination chamber;
    (ii) a sample retaining means;
    (iii) at least one fracturing means constructed and arranged to prepare on a sample a surface suitable for metallurgical analysis;
    (iv) a drying means constructed and arranged for slow drying of the sample in the selected ultra high vacuum condition;
    (v) a sealable outlet comprising connecting means selectively operatively connected to the inlet of the examination chamber; and
    (vi) a transporting means to transport the sample after surface preparation through a connecting means directly into the inlet of the examination chamber without leaving the selected ultra high vacuum condition.

2. A conditioning chamber device as claimed in claim 1 wherein the sample retaining means comprises a pedestal constructed and arranged to releasably secure a sample holder.

3. A conditioning chamber device as claimed in claim 2 wherein the transporting means comprises a transporter rod attached to the pedestal, and wherein movement of the transporter rod is regulated by an external control means.

4. A conditioning chamber device as claimed in claim 3 wherein the external control means comprises magnetic coupling.

5. A conditioning chamber device as claimed in claim 2, wherein the sample holder is a sample platen constructed and arranged to accommodate samples which are in a slurry condition.

6. A conditioning chamber device as claimed in claim 2, wherein the sample retaining means further comprises at least one gripping means constructed and arranged to retain the pedestal in at least one preselected position.

7. A conditioning chamber device as claimed in claim 1, wherein the vacuum pump means comprises a low vacuum roughing pump, a turbomolecular pump and an ion pump.

8. A conditioning chamber device as claimed in claim 7, wherein the low vacuum roughing pump is selected from a rotary vane pump, a dry scroll pump and a diaphragm pump.

9. A conditioning chamber device as claimed in claim 7, wherein the ion pump is selected from a triode ion pump, a diode ion pump and a star cell ion pump.

10. A conditioning chamber device as claimed in claim 1 wherein the fracturing means comprises a pair of chisels operable from substantially opposed directions in relation to each other.

11. A conditioning chamber device as claimed in claim 10 wherein each of the chisels has a cutting edge of tempered steel.

12. A conditioning chamber device as claimed in claim 1 wherein the transporting means comprises a transporter rod operatively secured to the sample retaining means, and wherein movement of the transporter rod is regulated by an external control means.

13. A conditioning chamber device as claimed in claim 12 wherein the external control means comprises magnetic coupling.

14. A conditioning chamber device as claimed in claim 12, wherein the sample retaining means comprises a gripping means and the transporter rod is permanently secured to the gripping means.

15. A method of conditioning a metallurgical sample for surface analysis by the steps of (i) providing a conditioning chamber device operatively and sealably connectable to an instrument having an examination chamber operable in an ultra high vacuum condition at a selected pressure below $10^{-7}$ Torr;
(ii) securing the sample within the conditioning chamber;
(iii) reducing the conditioning chamber to a selected ultra high vacuum condition corresponding with the selected pressure of the examination chamber;
(iv) drying the sample;
(v) fracturing the sample by a fracturing means to prepare a surface suitable for metallurgical analysis; and
(vi) sealably connecting the conditioning chamber to an inlet of the examination chamber and transporting the sample by a transporting means from the conditioning chamber directly into the examination chamber without leaving the selected ultra high vacuum condition.

16. A method as claimed in claim 15, wherein step (ii) comprises securing the sample on a sample supporting means, said sample supporting means being secured by a gripping means.

17. A method as claimed in claim 15, wherein step (iii) is performed by a low vacuum roughing pump, a turbomolecular pump and an ion pump.

18. A method as claimed in claim 15, wherein step (v) is performed by a pair of chisels operable from substantially opposed directions in relation to each other.

19. A method as claimed in claim 15, wherein step (vi) is performed by a transporter rod attached to the sample retaining means, and movement of the transporter rod is regulated by an external control means.

20. A method as claimed in claim 19, wherein the external control means comprises magnetic coupling.

21. A method as claimed in claim 16, wherein step (vi) is performed by a transporter rod attached to the gripping means, and movement of the transporter rod is regulated by an external control means.

22. A method as claimed in claim 21, wherein the external control means comprises magnetic coupling.

* * * * *